(12) United States Patent

Iwama et al.

(10) Patent No.: US 8,263,632 B2
(45) Date of Patent: Sep. 11, 2012

(54) AMINOPYRIDINE DERIVATIVES HAVING AURORA A SELECTIVE INHIBITORY ACTION

(75) Inventors: Toshiharu Iwama, Tsukuba (JP); Nobuhiko Kawanishi, Moriya (JP); Michael Mortimore, Abington (GB); Mitsuru Ohkubo, Ushiku (JP); Tomoko Sunami, Tokai-mura (JP)

(73) Assignees: Vertex Pharmaceuticals Incoporated, Cambridge, MA (US); MSD K.K., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/258,782

(22) PCT Filed: Mar. 15, 2010

(86) PCT No.: PCT/US2010/027283
§ 371 (c)(1),
(2), (4) Date: Sep. 22, 2011

(87) PCT Pub. No.: WO2010/111057
PCT Pub. Date: Sep. 30, 2010

(65) Prior Publication Data
US 2012/0015940 A1    Jan. 19, 2012

Related U.S. Application Data

(60) Provisional application No. 61/162,711, filed on Mar. 24, 2009.

(51) Int. Cl.
*C07D 401/04* (2006.01)
*A61K 31/535* (2006.01)

(52) U.S. Cl. ............ 514/375; 514/230.5; 544/105; 548/218

(58) Field of Classification Search ............ 544/105; 548/218; 514/230.5, 375
See application file for complete search history.

(56) References Cited

U.S. PATENT DOCUMENTS
7,319,106 B2 *    1/2008   Schrimpf et al. ............. 514/300
* cited by examiner

*Primary Examiner* — Kahsay T Habte
(74) *Attorney, Agent, or Firm* — Yong Zhao; David A. Muthard; Matthew A. Leff

(57) ABSTRACT

The present invention relates to a compound of Formula (I):

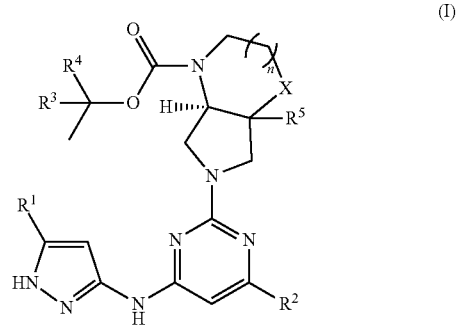

wherein: n is 0 or 1; X is O or $CH_2$; $R^1$ is H or $C_{1-2}$ alkyl; $R^2$ is H or $C_{1-3}$ alkyl; $R^3$ and $R^4$ are each independently H or $C_{1-2}$ alkyl, where the alkyl may be substituted with one to three of the same or different substituents selected from $R^{10}$; $R^5$ is H or $OCH_3$; $R^{10}$ is F or Cl; or a pharmaceutically acceptable salt or ester thereof

7 Claims, No Drawings

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Leu Arg Arg Ala Ser Leu Gly
 1               5

US 8,263,632 B2

AMINOPYRIDINE DERIVATIVES HAVING AURORA A SELECTIVE INHIBITORY ACTION

TECHNICAL FIELD

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

REFERENCE TO SEQUENCE LISTING SUBMITTED ELECTRONICALLY

The sequence listing of the present application is being submitted electronically via EFS-Web as an ASCII formatted sequence listing with a file name "BANONC00018USPCT-SEQTXT-21SEPT2011.txt", creation date of Sep. 21, 2011 and a size of 704 bytes. This sequence listing submitted via EFS-Web is part of the specification and is herein incorporated by reference in its entirety.

BACKGROUND ART

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

On the other hand, patent applications concerning compounds having an Aurora kinase inhibiting action have been previously filed (WO2002/022606, WO2002/022602, WO2002/0220601, W02006/046734).

DISCLOSURE OF THE INVENTION

The purpose of the present invention is to provide novel aminopyridine derivatives which show an excellent Aurora A selective inhibitory action and cell-growth inhibitory action based on the foregoing, thereby achieving a synergistic action by a combined use with other antitumor agent(s).

The present inventors have synthesized a variety of novel aminopyridine derivatives and found that the compound represented by the following Formula (I) shows an excellent Aurora A selective inhibitory action.

Thus, the invention relates to a compound of Formula (I):

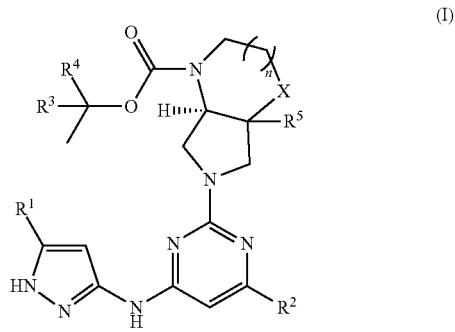

wherein:
n is 0 or 1;
X is O or $CH_2$;
$R^1$ is H or $C_{1-2}$ alkyl;
$R^2$ is H or $C_{1-3}$ alkyl;
$R^3$ and $R^4$ are each independently H or $C_{1-2}$ alkyl, where the alkyl may be substituted with one to three of the same or different substituents selected from $R^{10}$;
$R^5$ is H or $OCH_3$;
$R^{10}$ is F or Cl;
or a pharmaceutically acceptable salt or ester thereof.

The invention also relates to a combined preparation for simultaneous, separate or sequential administration in the treatment of cancer, comprising two separate preparations which are:

(i) a preparation comprising, together with a pharmaceutically acceptable carrier or diluent, a compound represented by the above-described Formula (I) or a pharmaceutically acceptable salt or ester thereof; and (ii) a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:

the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;

the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;

the antitumor antibiotic is actinomycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;

the plant-derived antitumor agent is vincristine, vinblastine, vindesine, etoposide, sobuzoxane, docetaxel, paclitaxel or vinorelbine;

the antitumor platinum coordination compound is cisplatin, carboplatin, nedaplatin or oxaliplatin;

the antitumor camptothecin derivative is irinotecan, topotecan or eamptothecin;

the antitumor tyrosine kinase inhibitor is gefitinib, imatinib, sorafenib, sunitinib, dasatinib,or erlotinib;

the monoclonal antibody is cetuximab, rituximab, bevacizumab, alerntuzumab or trastuzumab;

the interferon is interferon α, interferon α-2a, interferon α-2b, interferon β, interferon γ-1a or interferon γ-n1;

the biological response modifier is krestin, lentinan, sizofiran, picibanil or ubenimex; and the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivates, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "alkyl" is intended to include both branched and straight-chain saturated aliphatic hydrocarbon groups having the specified number of carbon atoms. For example, $C_{1-6}$, as in the term "$C_{1-6}$ alkyl" is defined to include groups having 1, 2, 3, 4, 5, or 6 carbons in a linear or branched arrangement. For example, the term "$C_{1-6}$ alkyl" specifically includes methyl, ethyl, n-propyl, i-propyl, n-butyl, t-butyl, i-butyl, pentyl, hexyl, and so on. Generally, the term "$C_{m-n}$ alkyl" is defined to include groups having m to n carbons in a linear or branched arrangement, where m and n each independently are an integer of 1 to 6 but n is greater than m.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovorin.

Here, in the above-mentioned combined preparation, either or both of the two separate preparations may be an oral preparation; and also one may be an oral preparation, while another may be a parental preparation (injections or drip infusions).

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known. Preferably, oral preparations, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably oral administration. Thus, when a combined preparation is administered, both administrations may be parenteral; one administration may be parenteral while the other may be oral; or both administrations may be oral. Preferably, both preparations in the combined preparation are administered orally. Here, the term "parenteral administration" is, for example, intravenous administration, subcutaneous administration or intramuscular administration, and preferably it is intravenous administration. Even when three or more preparations are combined and administered, every preparation may be orally administered.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel or docetaxel, preferably paclitaxel or docetaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms or by organic synthesis and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The term "plant-derived antitumor agent" may be exemplified by vincristine, vinblastine, vindesine, etoposide, sobuzoxane, docetaxel, paclitaxel and vinorelbine, and preferred are docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "antitumor platinum coordination (platinum-complex) compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediamine-malonatoplatinum (II); aqua(1,2-diaminodicyclohexane) sulfatoplatinum (II); aqua(1,2-diaminodicyclohexane)malonatoplatinum (II); (1,2-diaminocyclohexane) malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers a γ-phosphate group of ATP to a hydroxy group of a specific tyrosine in protein. The term "antitumor tyrosine kinase inhibitor" may be exemplified by gefitinib, imatinib, sorafenib, sunitinib, dasatinib, or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofiran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420, 319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from. Wyeth Corp. as Rapamune (tradename); and vairubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tadename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); sorafenib from Bayer as Nexavar (tradename); sunitinib from Pfizer as Sutent (tradename); dasatinib from Bristol Myers Squibb as Sprycel (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon a from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNIβ (tradename); interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofiran from Kaken Seiyaku Co., Ltd. as Sonifiran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from. Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group or a pyridine analogue group, any of which is substituted with an amino group. It is exemplified by a compound of the above Formula (I), and preferably any one compound of the below-mentioned (a) to (c): a compound which is:

(a) (2S)-1,1,1-trifluoropropan-2-yl(3aR,6aR)-3a-methoxy-5-[4-methyl-6-(1H-pyrazol-3-ylamino)pyrimidin-2-yl] hexahydropyrrolo[3,4-b]pyrrole-1(2H)-carboxylate, (b) (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate, or (c) 1,1,1-trifluoro-2-methylpropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate, or a pharmaceutically acceptable salt or ester thereof.

Embodiments of the compound represented by the above Formula (I) will be illustrated in more detail.

n is 0 or 1;
X is O or $CH_2$;
$R^1$ is H or $C_{1-2}$ alkyl.
Preferably, $R^1$ is H or methyl.
$R^2$ is H or $C_{1-3}$ alkyl.
Preferably, $R^2$ is H or methyl.
$R^3$ and $R^4$ are each independently H or $C_{1-2}$ alkyl, where the alkyl may be substituted with one to three of the same or different substituents selected from $R^{10}$.
Preferably, $R^3$ and $R^4$ are each independently H or methyl which may be substituted with one to three of the same or different substituents selected from $R^{10}$.
$R^5$ is H or $OCH_3$.
Preferably, $R^5$ is H.
$R^{10}$ is F or Cl.
Preferably, $R^{10}$ is F.

Further, in the combined preparation comprising two separate preparations according to the invention, preferably either or both of the two separate preparations are an oral preparation.

The combined preparation comprising two separate preparations according to the invention is preferably such that one of the preparations is a preparation containing, together with a pharmaceutically acceptable carrier or diluent, the following:

(a) (2S)-1,1,1-trifluoropropan-2-yl (3aR,6aR)-3a-methoxy-5-[4-methyl-6-(1H-pyrazol-3-ylamino)pyrimidin-2-yl]hexahydropyrrolo[3,4-b]pyrrole-1(2H)-carboxylate, (b) (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate, or (c) 1,1,1-trifluoro-2-methylpropan-2-yl (4aR,7aR)-6-[4-methyl-6-(1H-pyrazol-3-ylamino)pyrimidin-2-yl]hexahydropyrrolo[3,4-b][1,4] oxazine-4(4aH)-carboxylate, or a pharmaceutically acceptable salt or ester thereof; and the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains, together with a pharmaceutically acceptable carrier or diluent, the following:

(a) (2S)-1,1,1-trifluoropropan-2-yl (3aR,6aR)-3a-methoxy-5-[4-methyl-6-(1H-pyrazol-3-ylamino)pyrimidin-2-yl]hexahydropyrrolo[3,4-b]pyrrole-1(2H)-carboxylate, (b) (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate, or (c) 1,1,1-trifluoro-2-methylpropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate, or a pharmaceutically acceptable salt or ester thereof; and paclitaxel or docetaxel, or a pharmaceutically acceptable salt or ester thereof, together with a pharmaceutically acceptable carrier or diluent.

Description of the Process for Preparation of Compound of Formula (I)

Compounds represented by the Formula (I):

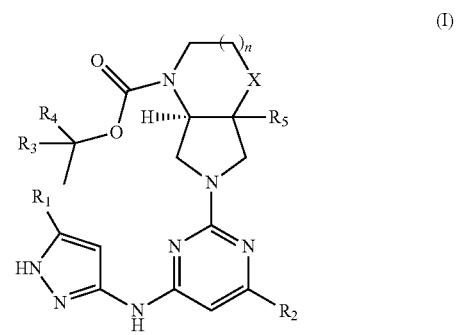

(wherein $R_1$, $R_2$, $R_3$, $R_4$ and $R_5$ have the same meaning as the symbols for the above Formula (I)) can be prepared by, for example, the following method. Hereinafter, the phrase "symbols for the above Formula (I)" as used herein means "the respective symbols as described for Formula (I) initially described in the present specification."

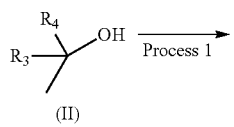

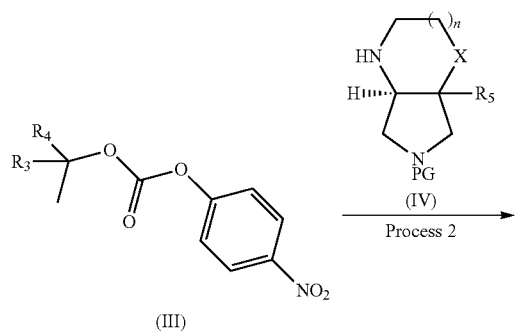

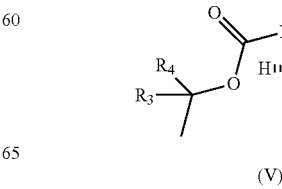

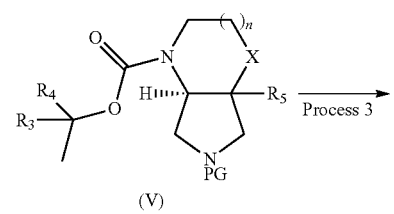

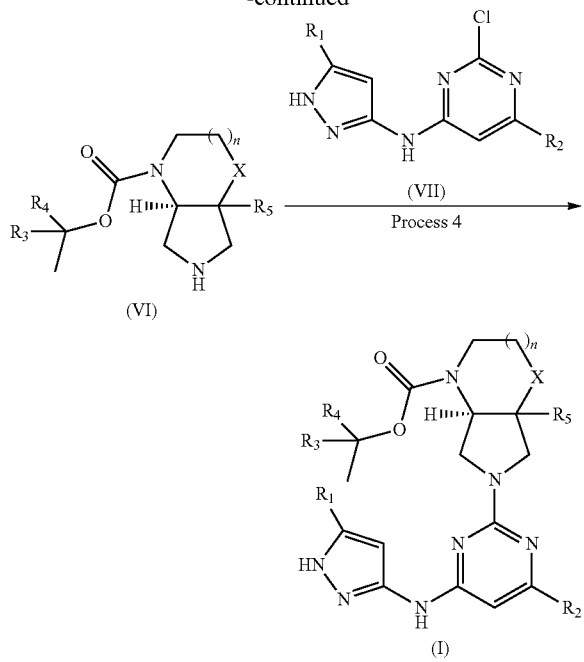

(Process 1)

The present process is a method of subjecting the Compound (II) (wherein $R_3$ and $R_4$ have the same meaning as the symbols for the above Formula (I)) and 4-nitrophenyl chloroformate, to an O-acylation reaction, thereby to produce Compound (III) (wherein $R_3$ and $R_4$ have the same meaning as the symbols for the above Formula (I)).

The Compound (II) used in this process may be exemplified by 2-trifluoromethyl-2-propanol, 1,1,1-trifluoro-2-propanol, and the like. The Compound (II) is commercially available or can be prepared by a known method.

The O-acylation reaction used in this process employs methods well known to those skilled in the art. In the O-acylation reaction used in this process, specifically, for example, the Compound (III) can be synthesized by reacting the Compound (II) in a solvent such as chloroform with a base such as pyridine, followed by adding thereto 4-nitrophenyl chloroformate. In this reaction, 4-nitrophenyl chloroformate is used in an amount of from 1 to 10 mol, preferably from 1 to 5 mol; and the base is used in an amount of from 1 to 10 mol, preferably from 1 to 5 mol, relative to 1 mol of Compound (II). The reaction temperature can be appropriately selected by a person having ordinary skill in the art in accordance with the starting compound or reaction solvent used, but it is typically from room temperature to 60° C. Also, the reaction is typically completed within 1 hour to 48 hours, but the reaction time can be appropriately extended or reduced.

The resulting Compound (III) is subjected to isolation and purification by known separation and purification means such as, for example, concentration, concentration under reduced pressure, crystallization, solvent extraction, reprecipitation or chromatography, or may be subjected to the next process without isolation and purification.

(Process 2)

The present process is a method of subjecting the Compound (III) (wherein $R_3$ and $R_4$ have the same meaning as the symbols for the above Formula (I)), obtained in the above-described Process 1, and Compound (IV) (wherein PG is a protective group such as benzyl and tert-butoxycarbonyl, and $R_5$ have the same meaning as the symbols for the above Formula (I)), to an alkoxycarbonylation reaction, thereby to produce Compound (V) (wherein PG is a protective group such as benzyl and tert-butoxycarbonyl, and $R_3$, $R_4$ and $R_5$ have the same meaning as the symbols for the above Formula (I)).

The Compound (IV) used in this process may be exemplified by (3S)-(+)-1-benzyl-3-aminopyrrolidine, tert-butyl (3R,4R)-3-amino-4-hydroxypyrrolidine-1-carboxylate, and the like. The Compound (IV) is commercially available or can be prepared by a known method.

The alkoxycarbonylation reaction used in this process employs methods well known to those skilled in the art. In the alkoxycarbonylation reaction used in this process, specifically, for example, the Compound (V) can be synthesized by reacting the Compound (III) in a solvent such as chloroform with a base such as N,N-diisopropylethylamine, followed by adding thereto the Compound (IV). In this reaction, Compound (IV) is used in an amount of from 1 to 10 mol, preferably from 1 to 5 mol; and the base is used in an amount of from 1 to 10 mol, preferably from 1 to 5 mol, relative to 1 mol of Compound (III). The reaction temperature can be appropriately selected by a person having ordinary skill in the art in accordance with the starting compound or reaction solvent used, but it is typically from room temperature to 60° C. Also, the reaction is typically completed within 1 hour to 48 hours, but the reaction time can be appropriately extended or reduced.

The resulting Compound (V) is subjected to isolation and purification by known separation and purification means such as, for example, concentration, concentration under reduced pressure, crystallization, solvent extraction, reprecipitation or chromatography, or may be subjected to the next process without isolation and purification.

(Process 3)

The present process is a method of deprotecting a protective group PG of the Compound (V) (wherein PG is a protective group such as benzyl and tert-butoxycarbonyl, and $R_3$, $R_4$ and $R_5$ have the same meaning as the symbols for the above Formula (I)), obtained in the above-described Process 2, thereby to produce Compound (VI) (wherein $R_3$, $R_4$ and $R_5$ have the same meaning as the symbols for the above Formula (I)).

For the deprotection reaction of PG, the method may vary depending on the type of the protective group or stability of the compound, but methods described in the literature [See T.W. Greene, Protective Groups in Organic Synthesis, John Wiley & Sons (1981)] or methods equivalent thereto can be carried out. For example, the Compound (V) in which PG is tert-butoxycarbonyl can be deprotected in a mixed solvent of trifluoroacetic acid and chloroform. The reaction temperature can be appropriately selected by a person having ordinary skill in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (VI) is subjected to isolation and purification by known separation and purification means such as, for example, concentration, concentration under reduced pressure, crystallization, solvent extraction, reprecipitation or chromatography, or may be subjected to the next process without isolation and purification.

(Process 4)

The present process is a method of subjecting the Compound (VI) (wherein $R_3$, $R_4$ and $R_5$ have the same meaning as the symbols for the above Formula (I)), obtained in the above-described Process 3, and Compound (VII) (wherein $R_1$ and $R_2$ have the same meaning as the symbols for the above Formula (I)), to an amination reaction, thereby to produce Compound (I) (wherein $R_1$, $R_2$, $R_3$, $R_4$ and $R_5$ have the same meaning as the symbols for the above Formula (I)).

The Compound (VII) used in this process may be exemplified by, 2-chloro-6-methyl-N-(5-methyl-1H-pyrazol-3-yl)pyrimidin-4-amine, 2-chloro-6-methyl-N-(1H-pyrazol-3-yl)pyrimidin-4-amine, and the like. The Compound (VII) can be prepared by a known method.

The amination reaction used in this process employs methods well known to those skilled in the art. In the amination reaction used in this process, specifically, for example, the Compound (I) can be synthesized by reacting the Compound (VI) in a solvent such as dimethylsulfoxide with a base such as N,N-diisopropylethylamine, followed by adding thereto the Compound (VII). In this reaction, Compound (VII) is used in an amount of from 1 to 10 mol, preferably from 1 to 5 mol; and the base is used in an amount of from 1 to 10 mol, preferably from 1 to 5 mol, relative to 1 mol of Compound (VI). The reaction temperature can be appropriately selected by a person having ordinary skill in the art in accordance with the starting compound or reaction solvent used, but it is typically from room temperature to 100° C. Also, the reaction is typically completed within 1 hour to 48 hours, but the reaction time can be appropriately extended or reduced.

The resulting Compound (I) is subjected to isolation and purification by known separation and purification means such as, for example, concentration, concentration under reduced pressure, crystallization, solvent extraction, reprecipitation or chromatography, or may be subjected to the next process without isolation and purification.

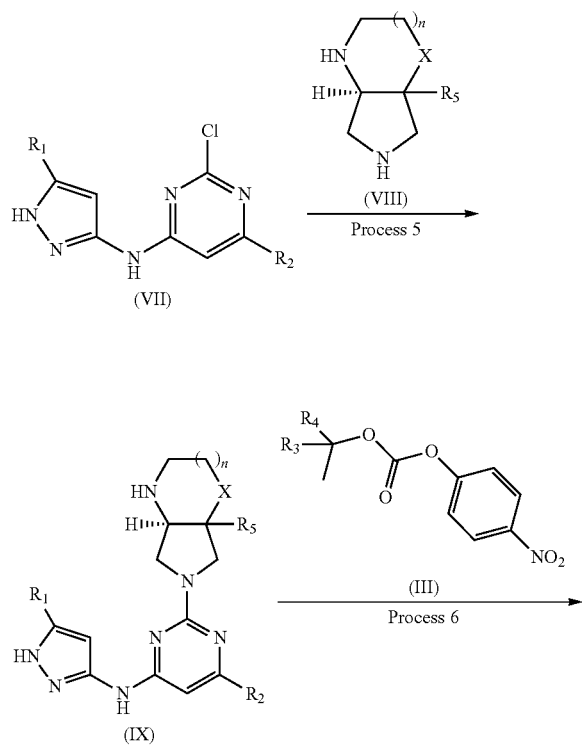

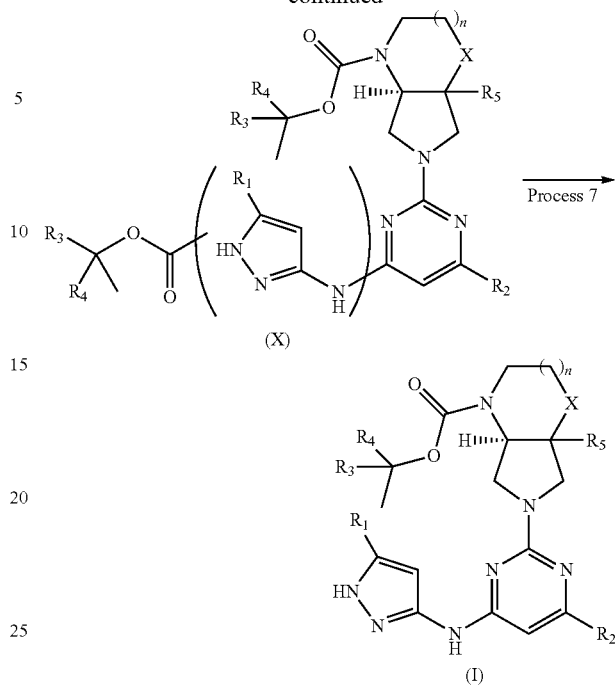

Compounds represented by the Formula (I) (wherein $R_1$, $R_2$, $R_3$, $R_4$ and $R_5$ have the same meaning as the symbols for the above Formula (I)) can be also prepared by, for example, the following method.

(Process 5)

The present process is a method of subjecting the Compound (VII) (wherein $R_1$ and $R_2$ have the same meaning as the symbols for the above Formula (I)) and Compound (VIII) (wherein $R_5$ has the same meaning as the symbols for the above Formula (I)), to an amination reaction, thereby to produce Compound (IX) (wherein $R_1$, $R_2$ and $R_5$ have the same meaning as the symbols for the above Formula (I)).

The Compound (VII) used in this process may be exemplified by, 2-chloro-6-methyl-N-(5-methyl-1H-pyrazol-3-yl)pyrimidin-4-amine, 2-chloro-6-methyl-N-(1H-pyrazol-3-yl)pyrimidin-4-amine, and the like. The Compound (VII) can be prepared by a known method.

The Compound (VIII) used in this process may be exemplified by, (3S,4R)-4-methylpyrrolidin-3-amine, (4aR,7aR)-octahydropyrrolo[3,4-b][1,4]oxazine, and the like. The Compound (IV) is commercially available or can be prepared by a known method.

The amination reaction used in this process employs methods well known to those skilled in the art. In the amination reaction used in this process, specifically, for example, the Compound (IX) can be synthesized by reacting the Compound (VII) in a solvent such as dimethylsulfoxide with a base such as N,N-diisopropylethylamine, followed by adding thereto the Compound (VIII). In this reaction, Compound (VIII) is used in an amount of from 1 to 10 mol, preferably from 1 to 5 mol; and the base is used in an amount of from 1 to 10 mol, preferably from 1 to 5 mol, relative to 1 mol of Compound (IV). The reaction temperature can be appropriately selected by a person having ordinary skill in the art in accordance with the starting compound or reaction solvent used, but it is typically from room temperature to 120° C. Also, the reaction is typically completed within 1 hour to 48 hours, but the reaction time can be appropriately extended or reduced.

The resulting Compound (IX) is subjected to isolation and purification by known separation and purification means such as, for example, concentration, concentration under reduced pressure, crystallization, solvent extraction, reprecipitation or chromatography, or may be subjected to the next process without isolation and purification.

(Process 6)

The present process is a method of subjecting the Compound (IX) (wherein $R_1$, $R_2$ and $R_5$ have the same meaning as the symbols for the above Formula (I)), obtained in the above-described Process 5, and Compound (III) (wherein $R_3$ and $R_4$ have the same meaning as the symbols for the above Formula (I)), obtained in the above-described Process 1, to an di-alkoxycarbonylation reaction, thereby to produce Compound (X) (wherein $R_1$, $R_2$, $R_3$, $R_4$ and $R_5$ have the same meaning as the symbols for the above Formula (I)).

The di-alkoxycarbonylation reaction used in this process employs methods well known to those skilled in the art. In the di-alkoxycarbonylation reaction used in this process, specifically, for example, the Compound (X) can be synthesized by reacting the Compound (IX) in a solvent such as chloroform with a base such as N,N-diisopropylethylamine, followed by adding thereto the Compound (III). In this reaction, Compound (III) is used in an amount of from 2 to 20 mol, preferably from 2 to 10 mol; and the base is used in an amount of from 2 to 20 mol, preferably from 2 to 10 mol, relative to 1 mol of Compound (IX). The reaction temperature can be appropriately selected by a person having ordinary skill in the art in accordance with the starting compound or reaction solvent used, but it is typically from room temperature to 60° C. Also, the reaction is typically completed within 1 hour to 48 hours, but the reaction time can be appropriately extended or reduced.

The resulting Compound (X) is subjected to isolation and purification by known separation and purification means such as, for example, concentration, concentration under reduced pressure, crystallization, solvent extraction, reprecipitation or chromatography, or may be subjected to the next process without isolation and purification.

(Process 7)

The present process is a method for the hydrolysis of the Compound (X) (wherein $R_1$, $R_2$, $R_3$, $R_4$ and $R_5$ have the same meaning as the symbols for the above Formula (I)), obtained in the above-described Process 6, thereby to produce Compound (I) (wherein $R_1$, $R_2$, $R_3$, $R_4$ and $R_5$ have the same meaning as the symbols for the above Formula (I)).

The hydrolysis used in this process employs methods well known to those skilled in the art. In the hydrolysis reaction used in this process, specifically, for example, the Compound (I) can be synthesized by reacting the Compound (X) in a solvent such as methanol with a base such as potassium carbonate. In this reaction, the base is used in an amount of from 2 to 20 mol, preferably from 2 to 10 mol, relative to 1 mol of Compound (I). The reaction temperature can be appropriately selected by a person having ordinary skill in the art in accordance with the starting compound or reaction solvent used, but it is typically from 0° C. to room temperature. Also, the reaction is typically completed within 1 hour to 48 hours, but the reaction time can be appropriately extended or reduced.

The resulting Compound (I) is subjected to isolation and purification by known separation and purification means such as, for example, concentration, concentration under reduced pressure, crystallization, solvent extraction, reprecipitation or chromatography, or may be subjected to the next process without isolation and purification.

Next, the Aurora A and Aurora B inhibitory actions of the compound of General Formula (I) according to the invention will be explained below.

Aurora A Inhibitory Action (1) Purification of Aurora A cDNA of Aurora A having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of activity of Aurora A

For measurement of the activity of Aurora A, the substrate used was Kemptide (Leu-Arg-Arg-Ala-Ser-Leu-Gly) (SEQ. ID. NO.: 1), a synthetic peptide purchased from Sigma-Aldrich, Inc. [Certificate of analysis (Upstate, Inc.)].

Reaction was conducted by a partial modification of a method by Upstate, Inc. [Kinase Profiler™ Assay Protocols]. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora A, 100 µM of a substrate peptide, 20 µM of unlabeled adenosine triphosphate (ATP) and 0.5 µCi of [$\gamma$-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [$\gamma$-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

Aurora B Inhibitory Action (1) Purification of Aurora B cDNA of Aurora B having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of activity of Aurora B

For measurement of the activity of Aurora B, the substrate used was Kemptide (Leu-Arg-Arg-Ala-Ser-Leu-Gly) (SEQ. ID. NO.: 1), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora B, 100 µM of a substrate peptide, 100 µM of unlabeled adenosine triphosphate (ATP) and 1 µCi of [$\gamma$-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

TABLE 1

| Example | Inhibitory activity for Aurora A ($IC_{50}$, nM) | Inhibitory activity for Aurora B ($IC_{50}$, nM) |
|---|---|---|
| Example 1 | 2.3 | 730 |
| Example 2 | 1.3 | 85 |
| Example 3 | 5.4 | 870 |

From the above, the compound according to the invention is believed to be useful as an antitumor agent since it exhibits excellent Aurora A selective inhibitory activity, leading to a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the Formula (I), the type of the compound represented by the Formula (I) used, and the dosage form of the compound represented by the Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The therapeutic unit for sorafenib is such that, for example, 200 mg is orally administered twice a day (400 mg per day) at least 1 hour before or 2 hours after eating.

The therapeutic unit for sunitinib is such that, for example, 50 mg is orally administered once a day for four weeks, followed by 2 weeks off.

WORKING EXAMPLES

In a thin-layer chromatography of Examples and Referential Examples, Silica gel 60 F254 (Merck) and Chromatolex NH (Fuji Silysia Chemical) was used as a plate and a UV detector was used in a detecting method. As pre-packed silica gel column for the chromatography, Biotage KP-Sil FLASH Cartridge (Biotage) or Purif-Pack Si (Moritex) were used. And KP-NH FLASH Cartridge (Biotage) or Purif-Pack NH (Moritex) was used for basic silica gel column chromatography. In a reversed phase preparative high performance liquid chromatography, XBridge Prep C18 (30×50 mm) (Waters) was used as a column, and a 0.1% aqueous trifluoroacetic acid solution and a 0.1% solution of trifluoroacetic acid in acetonitrile were used in a mobile phase. ESI-MS spectra were measured using micromass ZQ (Micromass). NMR spectra were measured using a spectrometer in a type of AL 400 (400 MHz; JEOL) and Inova 600 (600 MHz; Varian). For microwave reaction was used Initiator (Biotage).

Meanings of abbreviations used in the NMR measurement are as follows.

| | |
|---|---|
| s: | singlet |
| d: | doublet |
| dd: | double doublet |
| t: | triplet |
| dt: | double triplet |
| tt: | triple triplet |
| q: | quartet |
| m: | multiplet |
| br: | broad |
| brs: | broad singlet |
| Hz: | hertz |
| DMSO-d$_6$: | dimethylsulfoxide-d$_6$ |
| CDCl$_3$: | chloroform-d |
| CD$_3$OD: | methanol-d$_4$ |

Meanings of abbreviations used in experimental section are as follows.

| | |
|---|---|
| Boc: | tert-butoxycarbonyl group |
| dba: | dibenzylideneacetone |
| DIEA: | N,N-diisopropylethylamine |
| DMF: | N,N-dimethylformamide |
| DMSO: | dimethylsulfoxide |
| dppf: | 1,1'-bis(diphenylphosphino)ferrocene |
| EDCI • HCl: | N-[2-(dimethylamino)ethyl]N'-ethylcarbodiimide hydrochloride |
| EtOAc: | ethyl acetate |
| HOBt • H2O: | 1H-benzotriazole monohydrate |
| Me: | methyl group |
| MeOH: | methanol |
| Ms: | methanesulfonyl group |
| MsCl: | methanesulfonyl chloride |
| NMP: | N-methylpyrrolidone |
| PPh$_3$: | triphenylphosphine |
| RP-HPLC: | reverse phase high performance liquid chromatography |
| PTLC: | preparative thin layer chromatography |
| TEA: | triethylamine |
| TPA: | 2,2,2-trifluoroacetic acid |
| THF: | tetrahydrofuran |

Example 1

Preparation of (2S)-1,1,1-trifluoropropan-2-yl (3aR, 6aR)-3a-metboxy-5-[4-methyl-6-(1H-pyrazol-3-ylamino)pyrimidin-2-yl]hexahydropyrrolo[3,4-b]pyrrole-1(2H)-carboxylate

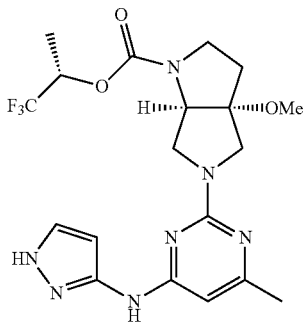

Step 1: Preparation of tert-butyl (3S)-3-(tert-butyldimethylsilyl)oxy-4-oxopyrrolidine-1-carboxylate

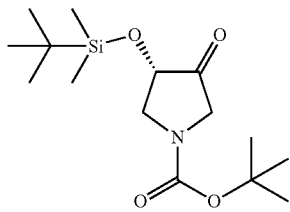

To a solution of oxalyl chloride (0.51 mL) in $CH_2Cl_2$ (7.3 mL) was added a 4.0M $CH_2Cl_2$ solution of DMSO (0.86 mL) at −78° C. After 10 min, a solution of tert-butyl (3S,4S)-3-hydroxy-4-(tert-butyldimethylsilyl)oxypyrrolidine-1-carboxylate (920 mg) in $CH_2Cl_2$ (5.8 mL) was added, and the mixture was stirred for 2 hours at −45° C. Triethylamine (3.25 mL) was added, and after being stirred for 10 min at room temperature, water was added. The mixture was separated, and the aqueous layer was extracted with ether. The combined organic layer was washed with brine, and dried over $MgSO_4$ and concentrated. The residue was purified with silica gel column chromatography (eluent: hexane/EtOAc=1/0~50/50) to give tert-butyl (3S)-3-(tert-butyldimethylsilyl)oxy-4-oxopyrrolidine-1-carboxylate as a pale yellow foam.

Step 2: Preparation of tert-butyl (3R,4S)-3-hydroxy-4-(tert-butyldimethylsilyl)oxy-3-(prop-2-en-1-yl)pyrrolidine-1-carboxylate

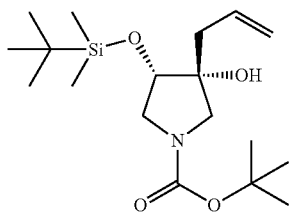

To an ice-cooled solution of tert-butyl (3S)-3-(tert-butyldimethylsilyl)oxy-4-oxopyrrolidine-1-carboxylate (1.2 g) in THF (5 mL) was added dropwise a 1M solution of allylmagnesium bromide in THF (3.8 mL), and the mixture was stirred for 30 min at 0° C. The reaction was quenched with saturated aqueous $NH_4Cl$ (5 mL) and the mixture was extracted with $Et_2O$. The extract was washed with brine, dried over $MgSO_4$, and concentrated in vacuo. The residue was purified with silica gel column chromatography (eluent: hexane/EtOAc=1/0~50/50) to give tert-butyl (3R,4S)-3-hydroxy-4-(tert-butyldimethylsilyl)oxy-3-(prop-2-en-1-yl)pyrrolidine-1-carboxylate as a pale yellow foam.

Step 3: Preparation of tert-butyl (3R,4S)-4-(tert-butyldimethylsilyl)oxy-3-methoxy-3-(prop-2-en-1-yl)pyrrolidine-1-carboxylate

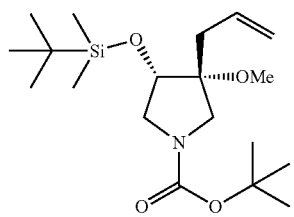

To a solution of tert-butyl (3R,4S)-3-hydroxy-4-(tert-butyldimethylsilyl)oxy-3-(prop-2-en-1-yl)pyrrolidine-1-carboxylate (550 mg) in DMF (10 mL) was added iodemethane (2.2 g) at 0° C. After 10 min, 60% NaH in oil (62 mg) was added, and the mixture was stirred for 1 hour at room temperature. The reaction was quenched with saturated aqueous $NH_4Cl$ and the mixture was extracted with $Et_2O$. The extract was washed with brine, dried over $MgSO_4$, and concentrated in vacuo. The residue was purified with silica gel column chromatography (eluent: hexane/EtOAc=1/0~50/50) to give tert-butyl (3R,4S)-4-(tert-butyldimethylsilyl)oxy-3-methoxy-3-(prop-2-en-1-yl)pyrrolidine-1-carboxylate as a pale yellow foam.

Step 4: Preparation of tert-butyl (3R,4S)-4-(tert-butyldimethylsilyl)oxy-3-(2-hydroxyethyl)-3-methoxy-pyrrolidine-1-carboxylate

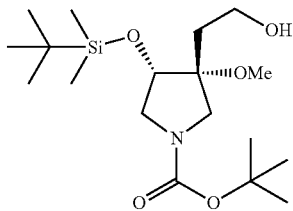

A solution of tert-butyl (3R,4S)-4-(tert-butyldimethylsilyl)oxy-3-methoxy-3-(prop-2-en-1-yl)pyrrolidine-1-carboxylate (230 mg) in $CH_2Cl_2$ (10 mL) was cooled to −78° C. and treated with a stream of ozone until a blue color persisted. A stream of nitrogen was passed through the solution for 15 minutes to remove excess ozone from solution. The solution was then treated with dimethylsulfide (0.2 mL) and allowed to warm to 23° C. over 30 min. Volatile components of the reaction mixture were removed in vacuo. The residue was dissolved in methanol (10 mL). To the solution was added NaBH₄ (50 mg) at 0° C. and the mixture was stirred at 0° C. for 30 minutes. The mixture was poured into saturated aqueous solution of NH₄Cl and extracted with CHCl₃. The extract was washed with brine, dried over MgSO₄ and concentrated. The residue was purified with silica gel column chromatography (eluent: hexane/EtOAc=99/1~1/99) to give tert-butyl (3R,4S)-4-(tert-butyldimethylsilyl)oxy-3-(2-hydroxyethyl)-3-methoxypyrrolidine-1-carboxylate as a pale yellow foam.

Step 5: Preparation of tert-butyl (3R,4S)-3-(2-azidoethyl)-4-hydroxy-3-methoxypyrrolidine-1-carboxylate

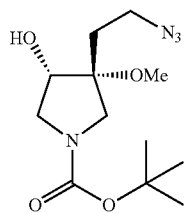

To the solution of tert-butyl (3R,4S)-4-(tert-butyldimethylsilyl)oxy-3-(2-hydroxyethyl)-3-methoxypyrrolidine-1-carboxylate (96 mg) in Et₂O (5 mL) was added DIEA (140 mg) and MSCl (60 mg) at room temperature. And the mixture was stirred at room temperature for 1 hour. After the period, the mixture was poured into saturated aqueous solution of NaHCO₃ and extracted with CHCl₃. The extract was dried over Na₂SO₄ and concentrated. The residue was dissolved into DMF (5 mL). To the solution was added NaN₃ (50 mg) and the mixture was heated to 90° C. under stirring overnight. The mixture was poured into saturated aqueous solution of NaHCO₃ and extracted with CHCl₃. The extract was dried over Na₂SO₄ and concentrated. The residue was dissolved in THF (2 mL), and then the solution was added into tetrabutylammonium fluoride (1M THF solution, 0.5 mL) under ice cooling. The mixture was stirred at room temperature at 2 hours, and then diluted with EtOAc and washed with brine, dried over MgSO₄, and then concentrated in vacuo. The residue was purified with silica gel column chromatography (eluent: hexane/EtOAc=99/1~50/50) to give 1-tent-butyl 3-methyl trans-5-azidopiperidine-1,3-dicarboxylate as a pale yellow foam.

Step 6: Preparation of tert-butyl (3aR,6aR)-3a-methoxyhexahydropyrrolo[3,4-b]pyrrole-5(1H)-carboxylate

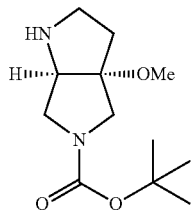

To the solution of tert-butyl (3R,4S)-3-(2-azidoethyl)-4-hydroxy-3-methoxypyrrolidine-1-carboxylate (85 mg) in CHCl₃ (5 mL) was added triethylamine (140 mg) and MsCl (50 mg) at room temperature. And the mixture was stirred at room temperature for 1 hour. After the period, the mixture was poured into saturated aqueous solution of NaHCO₃ and extracted with CHCl₃. The extract was dried over Na₂SO₄ and concentrated. The residue was dissolved in THF (5 mL). To the solution was added 10% palladium on activated carbon (20 mg). The resulting solution was placed under a H₂ atmosphere (balloon pressure) and stirred at room temperature for 15 hours. The solution obtained by filtration through Celite and washing the filter cake with MeOH was concentrated in vacuo. The residue was dissolved in CHCl₃ (3 mL) and refluxed for 1 day and then cooled to room temperature. The resulting mixture was purified with silica gel column chromatography (eluent: CHCl₃/MeOH=99/1~80/20) to give tert-butyl (3aR,6aR)-3a-methoxyhexahydropyrrolo[3,4-b]pyrrole-5(1H)-carboxylate as a pale yellow foam.

Step 7: Preparation of 5-tert-butyl 1-[(2S)-1,1,1-trifluoropropan-2-yl] (3aR,6aR)-3a-methoxyhexahydropyrrolo[3,4-b]pyrrole-1,5-dicarboxylate

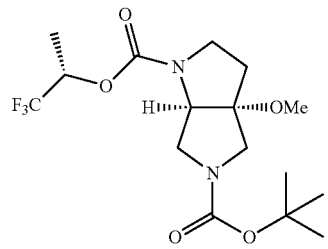

To a solution of 4-nitrophenyl (2S)-1,1,1-trifluoropropan-2-yl carbonate (15 mg) prepared in Referential Example 2 in CHCl₃ (2 mL) was added tert-butyl (3aR,6aR)-3a-methoxyhexahydropyrrolo[3,4-b]pyrrole-5(1H)-carboxylate (11 mg) at room temperature. The resulting mixture was stirred at 100° C. in a sealed tube for 2 hours and then cooled to room temperature. The mixture was purified with silica gel column chromatography (eluent: hexane/EtOAc=1/0~0/1) to give 5-tert-butyl 1-[(2S)-1,1,1-trifluoropropan-2-yl] (3aR,6aR)-3a-methoxyhexahydropyrrolo[3,4-b]pyrrole-1,5-dicarboxylate as a pale yellow foam.

Step 8: Preparation of (2S)-1,1,1-trifluoropropan-2-yl (3aR,6aR)-3a-methoxyhexahydropyrrolo[3,4-b]pyrrole-1(2H)-carboxylate

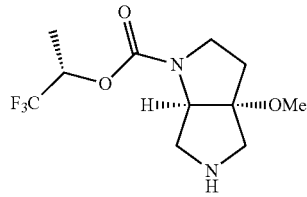

To the solution of 5-tert-butyl 1-[(2S)-1,1,1-trifluoropropan-2-yl] (3aR,6aR)-3a-methoxyhexahydropyrrolo[3,4-b]pyrrole-1,5-dicarboxylate (15 mg) in CHCl₃ (0.5 mL) was added TFA (0.5 mL). After stirring for 1 hour at room temperature, the mixture was poured into saturated aqueous solution of NaHCO₃ and extracted with CHCl₃. The extract was dried over Na$_2$SO$_4$ and concentrated to give (2S)-1,1,1-trifluoropropan-2-yl (3aR,6aR)-3a-methoxyhexahydropyrrolo[3,4-b]pyrrole-1(2H)-carboxylate as a pale yellow foam.

Step 9: Preparation of (2S)-1,1,1-trifluoropropan-2-yl (3aR,6aR)-3a-methoxy-5-[4-methyl-6-(1H-pyrazol-3-ylamino)pyrimidin-2-yl]hexahydropyrrolo[3,4-b]pyrrole-1(2H)-carboxylate To a solution of (2S)-1,1,1-trifluoropropan-2-yl (3aR,6aR)-3a-methoxyhexahydropyrrolo[3,4-b]pyrrole-1(2H)-carboxylate (8 mg) in DMSO (1 mL) was added 2-chloro-6-methyl-N-(1H-pyrazol-3-yl)pyrimidin-4-amine (6 mg) prepared in Referential Example 1 and DIEA (10 mg) at room temperature. The resulting mixture was stirred at 120° C. for 15 hours and then cooled to room temperature. The mixture was purified with preparative RP-HPLC to give (2S)-1,1,1-trifluoropropan-2-yl (3aR,6aR)-3a-methoxy-5-[4-methyl-6-(1H-pyrazol-3-ylamino)pyrimidin-2-yl]hexahydropyrrolo[3,4-b)]pyrrole-1(2H)-carboxylate as a pale yellow solid.

$^1$H NMR (400 MHz, DMSO-d$_6$) δ 1.30-1.45 (3H, m), 1.95-2.31 (5H, m), 3.26 (3H, s), 3.40-4.20 (7H, m), 5.22-5.40 (1H, m), 5.95-6.72 (2H, m), 7.40-7.70 (1H, m), 9.35-9.58 (1H, m), 12.15 (1H, brs) ESI-MS m/z 456 [M+H]$^+$.

Example 2

Preparation of (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate

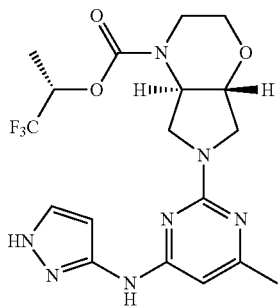

Step 1: Preparation of 2-[(4aR,7aR)-hexahydropyrrolo[3,4-b][1,4]oxazin-6(2H)-yl]-6-methyl-N-(1H-pyrazol-3-yl)pyrimidin-4-amine

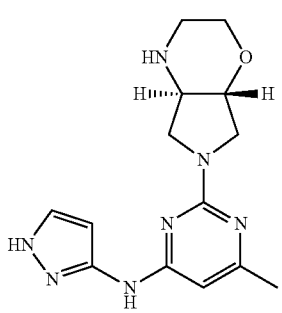

The title compound was prepared by the similar manner described in Step 9 of Example 1 by using (4aR,7aR)-octahydropyrrolo[3,4-b][1,4]oxazine instead of (2S)-1,1,1-trifluoropropan-2-yl (3aR,6aR)-3a-methoxyhexahydropyrrolo[3,4-b]pyrrole-1(2H)-carboxylate.

Step 2: Preparation of (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate

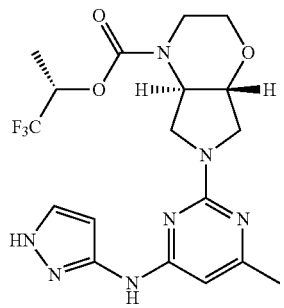

To a mixture of 2-[(4aR,7aR)-hexahydropyrrolo[3,4-b][1,4]oxazin-6(2H)-yl]-6-methyl-N-(1H-pyrazol-3-yl)pyrimidin-4-amine (20 mg) in CHCl$_3$ (3 mL) were added 4-nitrophenyl (2S)-1,1,1-trifluoropropan-2-yl carbonate (37 mg) prepared in Referential Example 2 and DIEA (30 mg) at room temperature. After 4-hour stirring at 100° C. in a sealed tube, the resulting mixture was cooled to room temperature and concentrated. The residue was diluted with MeOH (5 mL). To the resulting mixture was added potassium carbonate (100 mg) at 0° C. and stirred at 0° C. for 30 min. The mixture was poured into saturated aqueous solution of NH$_4$Cl and extracted with CHCl$_3$. The extract was washed with brine, dried over MgSO$_4$ and concentrated. The residue was purified with silica gel column chromatography (eluent: CHCl3/MeOH=99/1~80/20) to give (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate as a pale yellow foam.

ESI-MS m/z 442 [M+H]$^+$.

Example 3

1,1,1-trifluoro-2-methylpropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate

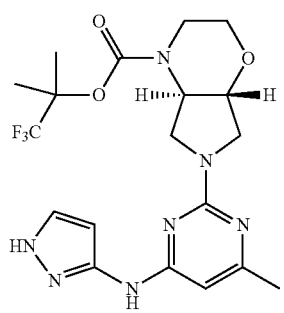

The title compound was prepared by the similar manner described in Step 2 of Example 2 by using 4-nitrophenyl 1,1,1-trifluoro-2-methylpropan-2-yl carbonate prepared in Referential Example 3 instead of 4-nitrophenyl (2S)-1,1,1-trifluoropropan-2-yl carbonate:

ESI-MS m/z 456 [M+H]$^+$.

REFERENTIAL EXAMPLES

Referential Example 1

Preparation of 2-chloro-6-methyl-N-(1H-pyrazol-3-yl)pyrimidin-4-amine

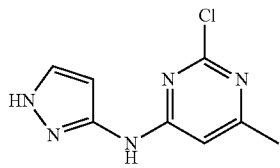

To the solution of 2,4-dichloro-6-methylpyrimidine (3.00 g) and 1H-pyrazol-3-amine (1.31 g) in NMP (30 mL) was added NaI (2.36 g) and DIEA (6.33 mL). And the mixture was heated to 80° C. under stirring. After 1 day, the mixture was cooled to room temperature. The mixture was diluted with Et$_2$O. The precipitate was collected by filtration, washed with the mixed solvent of hexane and EtOAc and dried in vacuo to give 2-chloro-6-methyl-N-(1H-pyrazol-5-yl)pyrimidin-4-amine (2.60 g) as a pale yellow solid.

Referential Example 2

4-nitrophenyl (2S)-1,1,1-trifluoropropan-2-yl carbonate

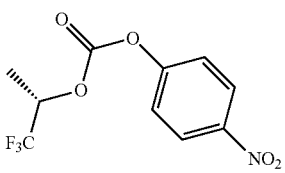

To a solution of (S)-(−)-1,1,1-trifluoro-2-propanol (1.95 g) in CHCl$_3$ (30 mL) was added 4-nitrophenyl chloroformate (5.16 g) and pyridine (1.35 g) at room temperature. After 1-hour stirring at 60° C., the resulting mixture was cooled to room temperature. To the resulting mixture was added 2-(dimethylamino)ethanol (1.52 g) and was stirred at room temperature for 1 hour. The mixture was poured into 1M aqueous solution of HCl and extracted with CHCl$_3$. The extract was washed with water and then dried over Na$_2$SO$_4$ and concentrated. The residue was purified with silica gel column chromatography (eluent: hexane/EtOAc=1/0~50/50) to give 4-nitrophenyl (2S)-1,1,1-trifluoropropan-2-yl carbonate as a pale yellow foam.

Referential Example 3

4-nitrophenyl 1,1,1-trifluoro-2-methylpropan-2-yl carbonate

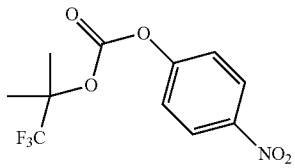

To a solution of 1,1,1-trifluoro-2-methylpropan-2-ol (1.0 g) in THF (30 mL) was added a 2M solution of n-butyl lithium in n-hexane (3.9 mL) and then 4-nitrophenyl chloroformate (2.4 g) at −75° C. The mixture was warmed to room temperature and diluted with ethyl acetate, washed with water, dried over sodium sulfate, filtered and concentrated in vacuo. The residue was purified by silica gel chromatography (0-50% EtOAc/Hexane) to give 4-nitrophenyl 1,1,1-trifluoro-2-methylpropan-2-yl carbonate as a pale yellow foam.

Industrial Applicability

The compound of the invention exhibits excellent Aurora A selective inhibitory action, and thus it is expected as a useful antitumor agent in the field of pharmaceuticals.

---

What is claimed is:

1. A compound of Formula (I):

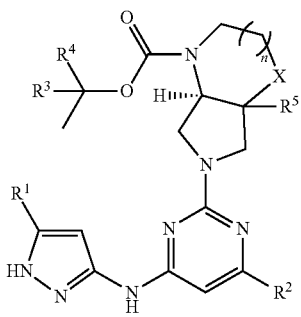

(I)

wherein:
n is 0 or 1;
X is O;
$R^1$ is H or $C_{1-2}$ alkyl;
$R^2$ is H or $C_{1-3}$ alkyl;
$R^3$ and $R^4$ are each independently H or $C_{1-2}$ alkyl, where the alkyl may be substituted with one to three of the same or different substituents selected from $R^{10}$;
$R^5$ is H or $OCH_3$; and
$R^{10}$ is F or Cl;
or a pharmaceutically acceptable salt or ester thereof 2. The compound according to claim 1 or a pharmaceutically acceptable salt or ester thereof, wherein $R^1$ is H or methyl.

3. The compound according to claim 2 or a pharmaceutically acceptable salt or ester thereof, wherein $R^2$ is H or methyl.

4. The compound according to claim 3 or a pharmaceutically acceptable salt or ester thereof, wherein $R^3$ and $R^4$ are each independently H or methyl which may be substituted with one to three of the same or different substituents selected from $R^{10}$; and
$R^{10}$ is F.

5. The compound according to claim 4 or a pharmaceutically acceptable salt or ester thereof, wherein the compound of Formula (I) is:

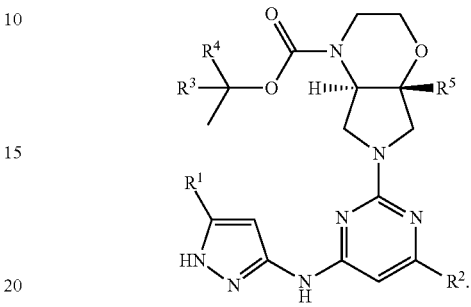

6. A compound which is:
(a) (2S)-1,1,1-trifluoropropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate; or
(b) 1,1,1-trifluoro-2-methylpropan-2-yl (4aR,7aR)-6-[4-methyl-6-(1H-pyrazol-3-ylamino)pyrimidin-2-yl]hexahydropyrrolo[3,4-b][1,4]oxazine-4(4aH)-carboxylate or a pharmaceutically acceptable salt or ester thereof.

7. A pharmaceutical composition comprising, together with pharmaceutically acceptable carrier or diluent, at least one compound according to claim 1 as active ingredient.

* * * * *